(12) United States Patent
Higuchi et al.

(10) Patent No.: US 6,254,531 B1
(45) Date of Patent: Jul. 3, 2001

(54) ELECTRONIC-ENDOSCOPE LIGHT QUANTITY CONTROLLING APPARATUS

(75) Inventors: Mitsuru Higuchi; Shinji Takeuchi; Kazuhiro Yamanaka, all of Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/264,240

(22) Filed: Mar. 8, 1999

(30) Foreign Application Priority Data

Mar. 10, 1998 (JP) .................................................. 10-078351
Mar. 10, 1998 (JP) .................................................. 10-078352

(51) Int. Cl.[7] ....................................................... A61B 1/06
(52) U.S. Cl. ........................ 600/178; 600/160; 600/180; 600/181; 248/68
(58) Field of Search .................................... 600/178–181, 600/109, 160; 348/68, 69; 362/574

(56) References Cited

U.S. PATENT DOCUMENTS 5,233,416 * 8/1993 Inoue ..................................... 348/70
5,984,862 * 11/1999 Honda et al. ......................... 600/180

* cited by examiner

*Primary Examiner*—John Mulcahy
(74) *Attorney, Agent, or Firm*—Snider & Associates; Ronald R. Snider

(57) ABSTRACT

The present invention is an electronic endoscope apparatus that can appropriately compensate for the lack of light quantity caused by a delayed response from a shielding mechanism in using the all-pixel reading system to form a high-quality image. In this apparatus, for a moving image, a pixel mix signal is read out from a CCD to reproduce motions faithfully. For a still image, to improve the image quality, a shielding period set by the shielding plate is used to read out all the pixels obtained by the CCD during a single exposure in order to form a pixel mix signal using a mixing circuit. A lamp characteristic memory stores table data indicating the characteristic between the lamp voltage of the current lamp and the quantity of outgoing light so that based on this data, a lamp voltage higher than in moving images is supplied to the lamp during the exposure for still-image formation. This configuration compensates for the lack of light quantity caused by a delayed response from the shielding plate to provide an appropriately bright still image. The lack of light quantity can also be compensated for by storing in the memory the characteristic between a diaphragm value and the outgoing light quantity and increasing the numerical aperture of the diaphragm based on the characteristic data.

8 Claims, 9 Drawing Sheets

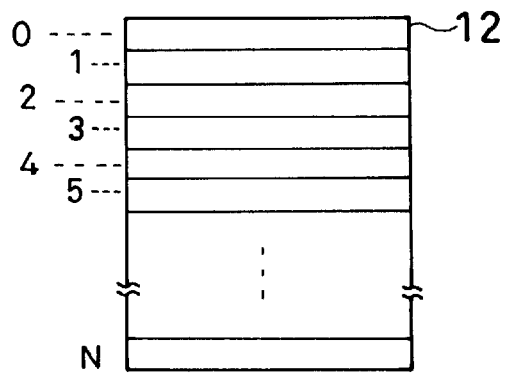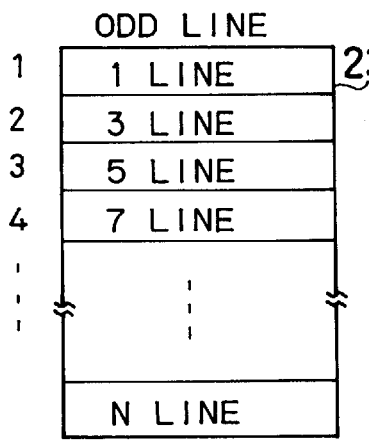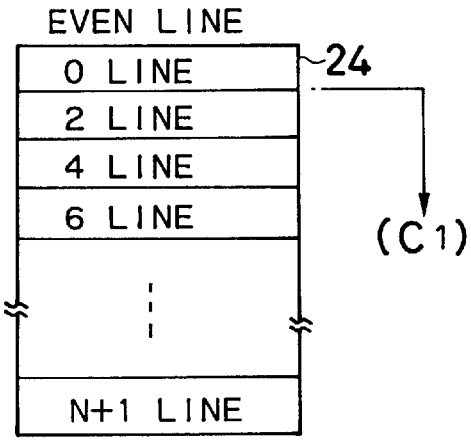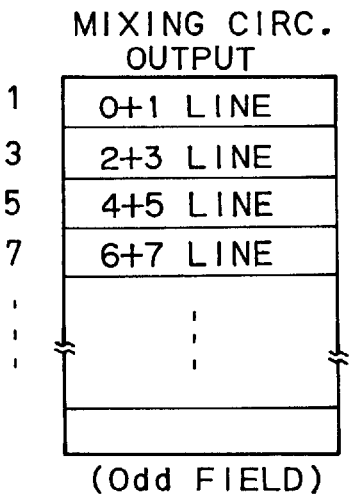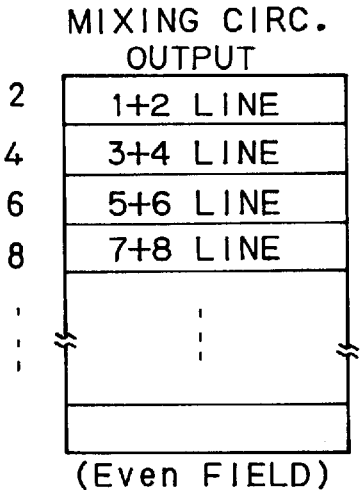

ELECTRONIC-ENDOSCOPE LIGHT QUANTITY CONTROLLING APPARATUS

BACKGROUND OF THE INVENTION

This application claims the priority of Japanese Patent Application Nos. 10-78351 and 10-78352 filed on Mar. 10, 1998 which are incorporated herein by reference.

1. Field of the Invention

The present invention relates to an electronic-endoscope controlling the quantity of light, and in particular, to the contents of light-quantity control for compensating for the lack of light quantity caused by the setting of a shielding period using an electronic endoscope executing an all-pixel reading system that uses the shielding period to read out all pixels accumulated in an image pickup device.

2. Description of the Prior Art

In an electronic endoscope apparatus, for example, CCD (Charge Coupled Device) is used as a solid image-pickup device, and this CCD is structured so as to obtain an image signal (video signal) by reading out charge accumulated in units of pixels by a photoelectric conversion device. In a simultaneous type electronic endoscope apparatus for example, color filters are arranged in units of pixels on the top surface of the forgoing CCD to thereby obtain a color image.

FIG. 9 shows an arrangement state for the forgoing color filters, and Mg (magenta) and Cy (cyan) pixels are arranged on an even line for example, andG (green) andYe (yellow) pixels are arranged on an odd line on a picked-up surface of CCD1 as shown. In this CCD1, accumulated charge (pixel signal) in units of pixels is to be obtained through these color filters.

According to a conventional color difference line sequential mix reading (pixel mix reading) system, accumulated charges of pixels on the upper and lower lines are added and mixed to be read out. For example, during the first exposure, video signals of such odd field as a mixed signal of 0-line and 1-line, a mixed signal of 2-line and 3-line, . . . are read out, and during the second exposure, video signals of such even field as a mixed signals of 1-line and 2-line, a mixed signal of 3-line and 4-line, . . . are read out. Therefore, two lines of mixed signals of CCD1 become one line of signals of field image, and one odd or even field of data are to be obtained by one exposure.

FIG. 10 shows an operation of signals read out from the foregoing CCD1, and in an electronic endoscope apparatus, an odd field and an even field are formed on the basis of the O (Odd)/E (Even) signal (field signal) for each 1/60 second (vertical synchronizing period) as shown in FIG. 10(A). Therefore, as shown in FIG. 10(B), signals are accumulated in accumulation (exposure) time T of an electronic shutter during the forgoing period of 1/60 second, and the accumulation mixed signal is read out during the next 1/60 second period. As a result, as shown in FIG. 10(C), an odd field signal, and an even field signal are to be obtained, and for example, the (n−1)th odd field signal becomes mixed signals of (0+1) line, (2+3) line, (4+5) line . . . which are shown on the left of FIG. 6, and the n-th even field signal becomes mixed signals of (1+2) line, (3+4) line, . . . which are shown on the right of FIG. 9.

These odd field signals and even field signals are interlace scanned to be formed as a one-frame image, and this image is displayed as a moving image on a monitor. Also, in the endoscope apparatus, a freeze switch is arranged in the operating unit, and when this freeze switch is depressed, a still image at the time is formed and displayed.

BRIEF SUMMARY OF THE INVENTION

Object of the Invention

In the foregoing simultaneous type electronic endoscope apparatus, however, there is a time lag of 1/60 second between those odd field image and even field image which are used to form the one-frame image as shown in the foregoing FIG. 10(C), and if there is a shake of the endoscope itself, a movement of the object to be observed or the like during this period of time, there is the problem that the image quality (resolution, color shift, etc.) will be deteriorated when the still image is displayed.

Thus, the applicant sets a predetermined light shielding period and uses an all-pixel reading system for reading all pixels out from data obtained during one exposure using this period. However, due to a delay in a mechanical (gear) response from, for example, a light shielding plate that sets the light shielding period, the exposure may be insufficient during the period of time required to read out all pixels. That is, complete light shielding conditions are required during the light shielding period required to read out data, so the light shielding plate is activated slightly before the beginning of the light shielding period in view of its response time. This response operation (the operation performed until complete light shielding is achieved) may cause lack of light quantity.

The present invention has been achieved in the light of this problem, and its object is to provide an electronic-endoscope light-quantity controlling apparatus that can appropriately compensate for the lack of light quantity caused by delayed responses from a light shielding mechanism, using an electronic endoscope adapted to form a high-quality image using the all-pixel reading system.

Summary of the Invention

In order to achieve this object, an electronic endoscope apparatus controlling the quantity of light according to this invention comprises a light source; an outgoing light quantity varying means for variably adjusting the quantity of outgoing light from the light source based on a predetermined control value; a shielding means for intercepting light from the light source and setting a shielding period for an all-pixel reading system; a signal processing circuit executing the all-pixel reading system that uses the shielding period to read out signals for all-pixels accumulated in an image pickup device during a single exposure; a storage means for storing characteristic data between the control value and the quantity of outgoing light; and a light quantity controlling means for controlling the outgoing light quantity adjusting means based on the characteristic data stored in the storage means to adjust the quantity of outgoing light from the light source, thereby compensating for the lack of light quantity caused by a delayed response from the shielding means for a shielding operation.

Another phase of the invention is characterized in that the outgoing light quantity varying means comprises a lamp driving means varies a lighting voltage for a light source lamp, in that the storage means stores the characteristic data between the lighting voltage for the light source lamp and the quantity of outgoing light, and in that the light quantity controlling means varies the lighting voltage for the light source lamp based on the characteristic data to adjust the quantity of outgoing light from the light source, thereby compensating for the lack of light quantity caused by a delayed response from the shielding means for a shielding operation. The characteristic data for the lamp include data for lamp voltage with give the necessary and sufficient quantity of outgoing light for the period in which all the picture elements are to be read.

Yet another phase of the invention is characterized in that the outgoing light quantity varying means comprises a diaphragm for adjusting the quantity of outgoing light from the light source lamp, in that the storage means stores the characteristic data between the diaphragm value of a diaphragm and the quantity of outgoing light, and in that the light quantity controlling means varies the numerical aperture of the diaphragm based on the characteristic data stored in the storage means to adjust the quantity of outgoing light from the light source, thereby compensating for the lack of light quantity caused by a delayed response from the shielding means for a shielding operation.

In each of these aspects of the invention, a light quantity sensor for detecting the quantity of outgoing light from the light source can be provided to store in the storage means the characteristic data on the lamp lighting voltage or the diaphragm value based on an output from the light quantity sensor.

In addition, the light quantity controlling means can execute a lamp or a diaphragm-value characteristic detection mode that uses the above optical sensor to automatically create and store the characteristic data on the diaphragm value.

Still another aspect of this invention is characterized in that this invention is applied to an electronic endoscope comprising the pixel mix reading system at the output of the image pickup device for mixing together pixels accumulated in the image pickup device in such a way that vertically arranged lines are mixed together and then outputting the resulting pixels to form a moving image and the all-pixel reading system for forming a still image by using the shielding period to read out all pixels accumulated in the image pickup device during a single exposure.

Next, how this configuration operates if the all-pixel reading system is executed only during the formation of a still image will be described. When a freeze switch is depressed, the all-pixel reading system is selected to form a still image. During a predetermined (the first) period of 1/60 second (a vertical synchronizing period), charges are accumulated due to exposure (the exposure time is arbitrary), and during the second period (1/60 second), the odd lines in the image pickup device (CCD) are read out and stored in a predetermined memory. During the third period (1/60 second), the remaining even lines are read out and stored in a predetermined memory.

To allow the even lines to be read out, the light shielding means intercepts light from a light source during the second period. That is, if, during the second period during which accumulated charges in the odd lines are sequentially read out, subsequent charges are accumulated, as in the prior art, the remaining even lines cannot be read out. Thus, this invention eliminates the optical output during the second period and reads out the accumulated charges in the even lines during the third period, thereby enabling a readout of signals for all the pixels in the image pickup device obtained during a single exposure.

Next, for example, video signals for the odd lines stored first in the memory are stored in a phase adjustment memory and are delayed by 1/60 second, and a mixing circuit then executes pixel mix processing between data for the odd and even lines. This image mix processing forms signals equivalent to those obtained by a pixel mix reading system operating when the image pickup device outputs signals, but is distinguished from this system in that it mixes pixels based on data obtained during a single exposure. Pixel mix signals are used to form odd and even field signals, and a still image is displayed based on these video signals. Thus, the still image is formed based on the signals for all pixels obtained during the single exposure and has a high quality.

On the other hand, in a normal condition under which the freeze switch is not pressed, the pixel mix reading system has been selected, and pixels in two horizontal lines read out from the image pickup device as in the prior art are mixed together and output to provide a moving image that reproduces motions of an object faithfully.

In the light shielding operation for still images, however, the light quantity may become insufficient during the exposure period for still-image formation due to, for example, a delayed mechanical response from the light shielding plate, as described above. Thus, based on the characteristic between the lighting voltage and outgoing light quantity of the current light source lamp that is stored in the storage means, the light-quantity controlling means according to this invention supplies a higher lamp lighting voltage than normal to the lamp during the exposure for still-image formation to provide an appropriate quantity of light in order to enable an appropriately bright still image to be obtained.

In addition, based on the characteristic between the diaphragm value (or an item that identifies the diaphragm value, for example, a diaphragm controlling voltage) and the quantity of outgoing light, the light controlling means according to another aspect of the invention reads out a diaphragm value that is higher than the current one by a predetermined quantity of light and supplies this diaphragm value data to the diaphragm driving circuit during the exposure for still-image formation to provide an appropriate quantity of light in order to enable an appropriately bright still image to be obtained.

Furthermore, the data on the lamp or diaphragm-value characteristic can be detected and stored upon the replacement of the lamp or at appropriate daily intervals using the optical sensor. Thus, these characteristics allow the type of the lamp such as a halogen or xenon lamp, differences among individual lamps, and the duration of service to be taken into account. As a result, an advantages is obtained that the lack of light quantity can be compensated for appropriately depending on the type of the lamp and the variation and secular change of the individual lamp.

BRIEF DESCRIPTION OF THE DRAWINGS

FIG. 2 shows image data read out between the CCD and the mixing circuit in FIG. 1;

DETAILED DESCRIPTION OF THE PREFERRED EMBODIMENTS

First Embodiment

Figure 1:
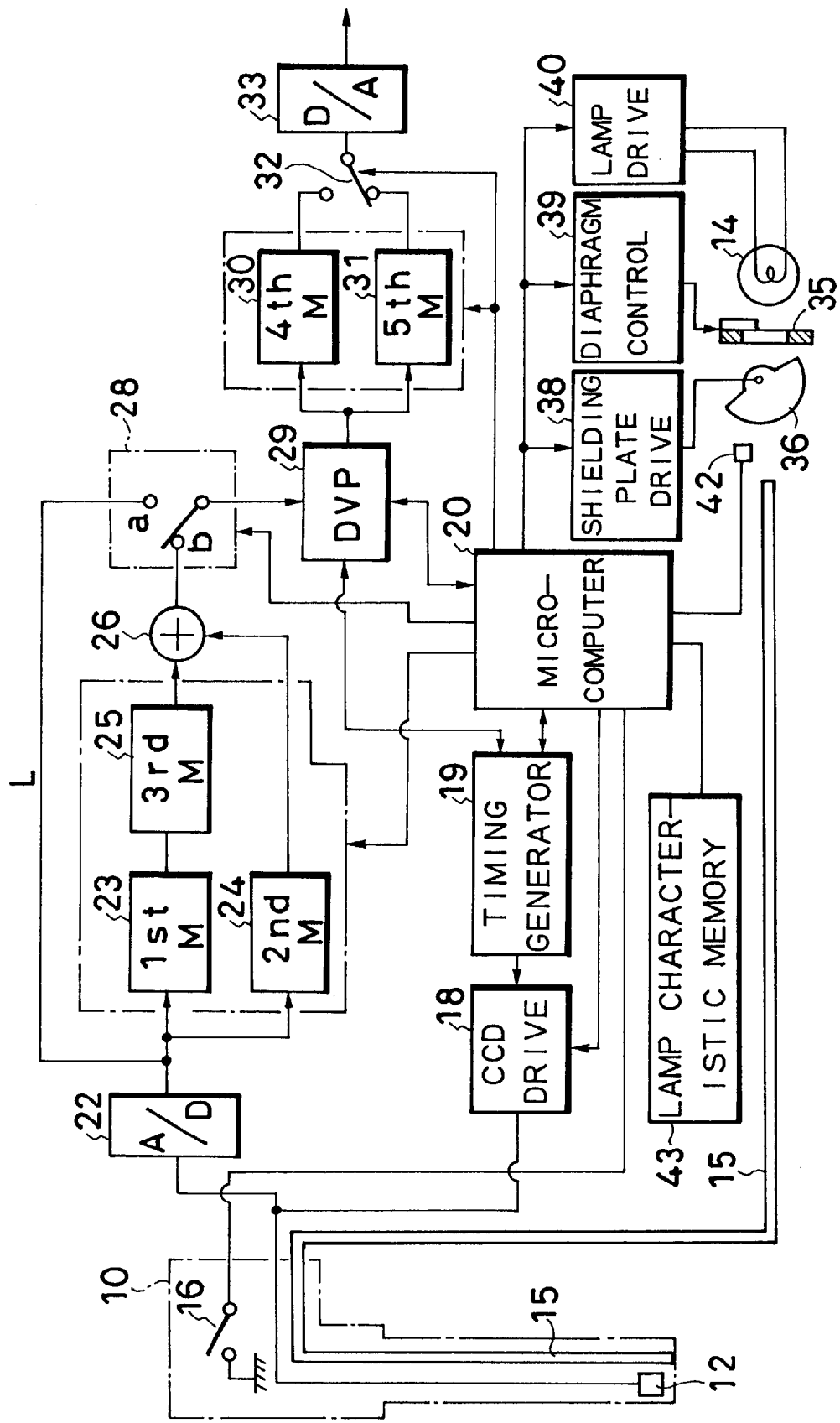
FIG. 1 is a block diagram showing the overall configuration of an electronic endoscope apparatus controlling the quantity of light according to a first embodiment of the present invention.

FIG. 1 shows a configuration of an electronic endoscope apparatus controlling the quantity of light according to a first embodiment. This electronic endoscope executes an all-pixel reading system for still images and controls a lamp voltage to compensate for the lack of light quantity. In FIG. 1, the apparatus has such a structure that a scope (electronic endoscope) 10 is connected to the processor device having an image processing circuit or a light source device. The scope 10 is provided with CCD12 at whose tip end portion the same color filters as described in FIG. 16 are arranged, and with a light guide 15 for guiding light from the light source 14 to the tip end portion. Also, an operating unit for the scope 10 is provided with a freeze switch 16 for displaying a still image.

To the foregoing CCD12, a CCD driving circuit 18 for driving it is connected, and to the driving circuit 18, there are connected a timing generator 19 and a microcomputer 20 that provides various controls. To the microcomputer 20, an operation signal from the foregoing freeze switch 16 is inputted. The foregoing CCD driving circuit 18 inputs a timing signal under the control of the microcomputer 20 to control the driving of the pixel mix reading system at the output of CCD for moving images and the all-pixel reading system for still images.

In the case of, for example, the all-pixel reading system, two types of pulses for driving accumulated data for all pixels, which have been accumulated in CCD12 by one exposure, into the odd line and the even line (staggering also temporarily) for reading out, are supplied from the foregoing CCD driving circuit 18, and on the basis of these pulses, control is performed so as to read out the foregoing odd line signals and even line signals from the CCD12 separately and successively. In this respect, one type read pulse is imparted to each line in the pixel mix reading system at the output of CCD.

In addition, the CCD12 there are provided a first memory 23 for storing image data of the foregoing odd line via an A/D converter 22 in order to read out all pixels, a second memory 24 for storing image data of the even line, a third memory 25 for phase adjustments for storing the data of the foregoing first memory 23 as they are and delaying the read timing by 1/60 second, and a mixing circuit for still image 26. That is, all pixel signals obtained at the CCD12 are divided into data of the odd line and data of the even line, and in this state, are once stored in the respective memories 23 and 24, but the odd line data of the first memory 23 are caused to be delayed by 1/60 second, whereby they are caused to have the same phase as the even line data stored in the second memory 24.

Thus, it becomes possible to read out both image data simultaneously, and in a mixing circuit 26 in the next stage, pixel data of the odd line in the third memory 25 and those of the even line in the second memory 24 can be added and mixed (pixel mixing process for still images). Therefore, in the case of still images, the same pixel mixed signal can be formed as the conventional color difference line sequential mix reading system by this mixing circuit 26.

FIG. 2 shows the content of still image data formed in a circuit from the foregoing CCD12 to the mixing circuit 26. As shown in FIG. 2(A), horizontal lines from 0-line to N-line are provided correspondingly to a number of scanning lines in the CCD12, and the structure is arranged so that the pixel data of these horizontal lines are transferred to a transfer line for reading out. The data of odd lines (1, 3, 5 . . . line) in the foregoing CCD12 are stored in the first memory 23 (and the third memory 25) in FIG. 2(B), and the data of even lines (2, 4, 6, . . . line) are stored in the second memory 24 in FIG. 2(C).

The data of these memories 25 and 24 are pixel-mixed between lines in FIGS. 2(B) and 2(C) by the mixing circuit 26 as described above, and as shown in FIG. 2(D), add operation data of 0-line+1-line, 2-line+3-line, 4-line+5-line, . . . are outputted as Odd field data. In a state in which the read line of FIG. 2(C) has been shifted underneath by one line (read out from a position indicated by C1 in the figure), they are pixel-mixed between lines in FIGS. 2(B) and 2(C). As shown in FIG. 2(E), add operation data of 1-line+2-line, 3-line+4-line, 5-line+6-line, . . . are outputted as even field data. In this respect, in this example, an odd number and an even number in lines of CCD12, and an odd number and an even number in fields for interlaced scanning are distinguished by representing them as ODD, EVEN, and Odd, Even, respectively.

In FIG. 1, at the subsequent stage of the forgoing mixing circuit 26, there is provided an image switching circuit 28 for switching between a moving image and a still image. An output from the A/D converter 22 is supplied to a terminal "a" of the image switching circuit 28 via a line L to form a moving image, while an output from the mixing circuit 26 is provided to its terminal "b". This image switching circuit 28 switches from terminal "a" to terminal "b" by the control of the microcomputer 20 when the forgoing freeze switch 16 is depressed. To the image switching circuit 28, there is connected a digital video processor (DVP) 29, and in this DVP 29, color signal processing using the same pixel mix reading system as before is performed, and for example, a color difference signal or a luminance signal is formed.

At the subsequent stage of this DVP 29, there are provided a fourth memory 30 for storing odd field data, a fifth memory 31 for storing even field data, a switching circuit 32 for switching between a terminal on the fourth memory 30 side and a terminal on the fifth memory 31 side, and a D/A converter 33. For example, for a still image, the fourth memory 30 stores odd field data comprising color difference signals into which the data in FIG. 2(D) has been converted, while the fifth memory 31 stores even field data comprising color difference signals into which the data in FIG. 2(E) has been converted.

On the other hand, in a light source unit for supplying light to a light guide 15 arranged in the foregoing scope 10, there are arranged a diaphragm 35 and a light shielding plate 36 (a shielding means) between the foregoing light source 14 and an incident end of the light guide 15. The light shielding plate 36 is constructed to rotate, for example, a semi-circular plate, and a driving circuit 38 is connected to rotationally drive the light shielding plate 36. In this example, the light shielding plate 36 intercepts light only for predetermined 1/60 second after the foregoing freeze switch 16 is depressed in a field O/E signal of a cycle of each 1/60 second.

Also, to the foregoing diaphragm 35, a diaphragm control circuit 39 is connected, and to the foregoing lamp 14, a lamp driving circuit 40 is connected. Furthermore, an optical sensor (a photo transistor) 42 is provided to measure the quantity of outgoing light from the light source, and a characteristics memory (EPROM or RAM) is provided to store table data (characteristics data) indicating the relationship between the quantity of outgoing light from the lamp 14 and the lamp voltage. The diaphragm controlling circuit 39 drives the diaphragm 35 based on an illuminance signal obtained by the DVP 29 in order to adjust the quantity of outgoing light from the light source. The lamp driving circuit 40, however, variably controls the lamp (lighting) voltage under the control of the microcomputer 20 in order to compensate for the lack of light quantity when a still image is selected. If a voltage Va is set nearly at 13 V when a moving image is selected, a voltage Vb is set between 13 and 15V when a still image is selected.

Figure 3:
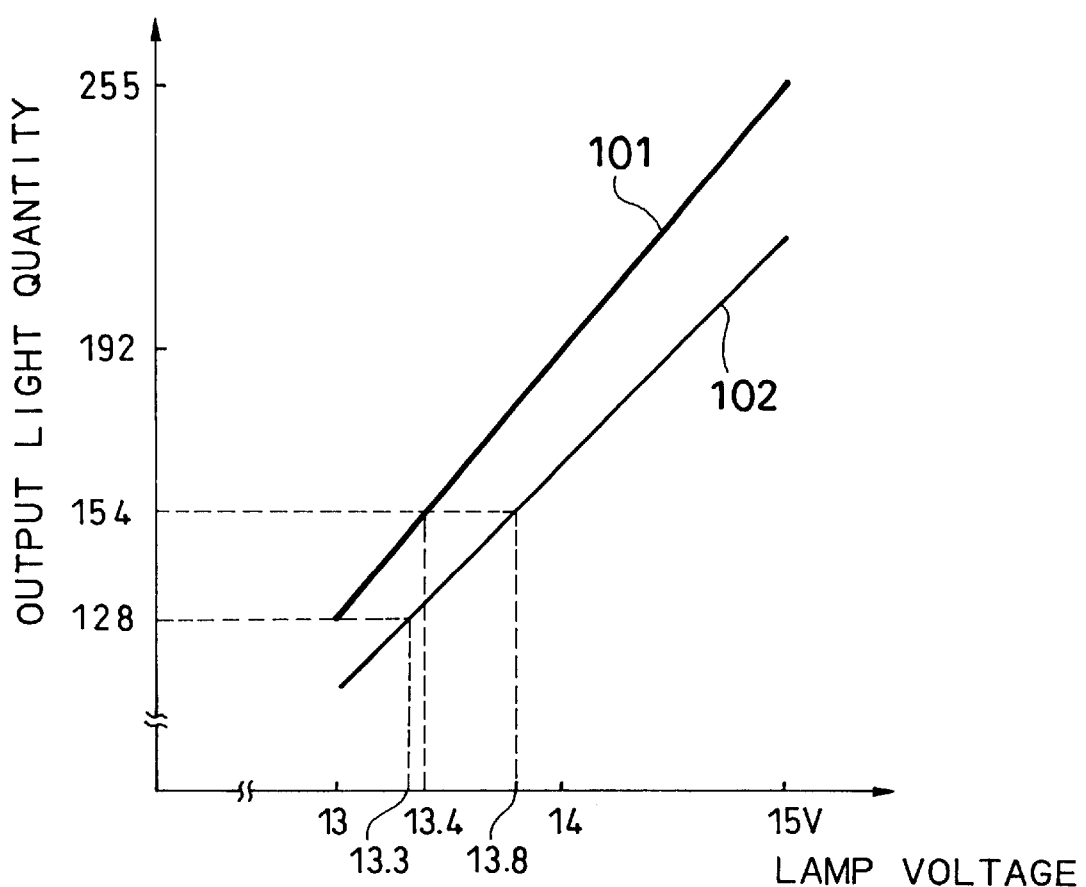
FIG. 3 is a graph showing a lamp characteristic according to the first embodiment.

That is, the apparatus executes a lamp characteristics detection mode at the replacement of the lamp or periodically, and uses the lamp driving circuit 40 to vary the lamp voltage between, for example, 13 and 15 V (this voltage and range are arbitrary) among 20 levels spaced at intervals of 0.1 V. The optical sensor 42 then detects the quantity of outgoing light from the light source, so that table data on the lamp characteristics such as that shown in FIG. 3 is stored in the characteristics memory 43. The value of light quantity detected by the optical sensor 42 is represented by digital values ranging from 0 to 255, and a linear (not necessarily linear) characteristic 101 is obtained wherein, for example, the light quantity value is 128 at 13 V and 255 at 15V. If the light quantity value 128 is optimal when a moving image is selected, the microcomputer 20 reads out 13 V as a normal lamp voltage (Va) of the lamp 14.

In addition, if the lack of light quantity is about 20% when a still image is selected, as shown in FIG. 3, the voltage of 13.8 V at the light quantity value of 154 that is larger than the value of 128 by 20% is read out from the characteristics memory 43 as a lamp voltage (Vb) for a still image. The microcomputer 20 supplies the data for the lamp voltages Va and Vb to the lamp driving circuit 40, so when the freeze switch 16 is depressed, the lamp voltage is increased from 13V up to 13.4 V to increase the quantity of outgoing light from the lamp 14 for a predetermined period of time (one field). This operation compensates for the lack of light quantity caused by a delayed response from the shielding plate 36 for the next shielding period.

The lamp characteristics memory 43 may store only data of the lamp voltage Va at the light quantity value of 128 required when a moving image is selected and the lamp voltage Vb at the light quantity value of 154 required when a still image is selected, instead of the table data for the characteristics in FIG. 3 (data sequence table).

Figure 4:
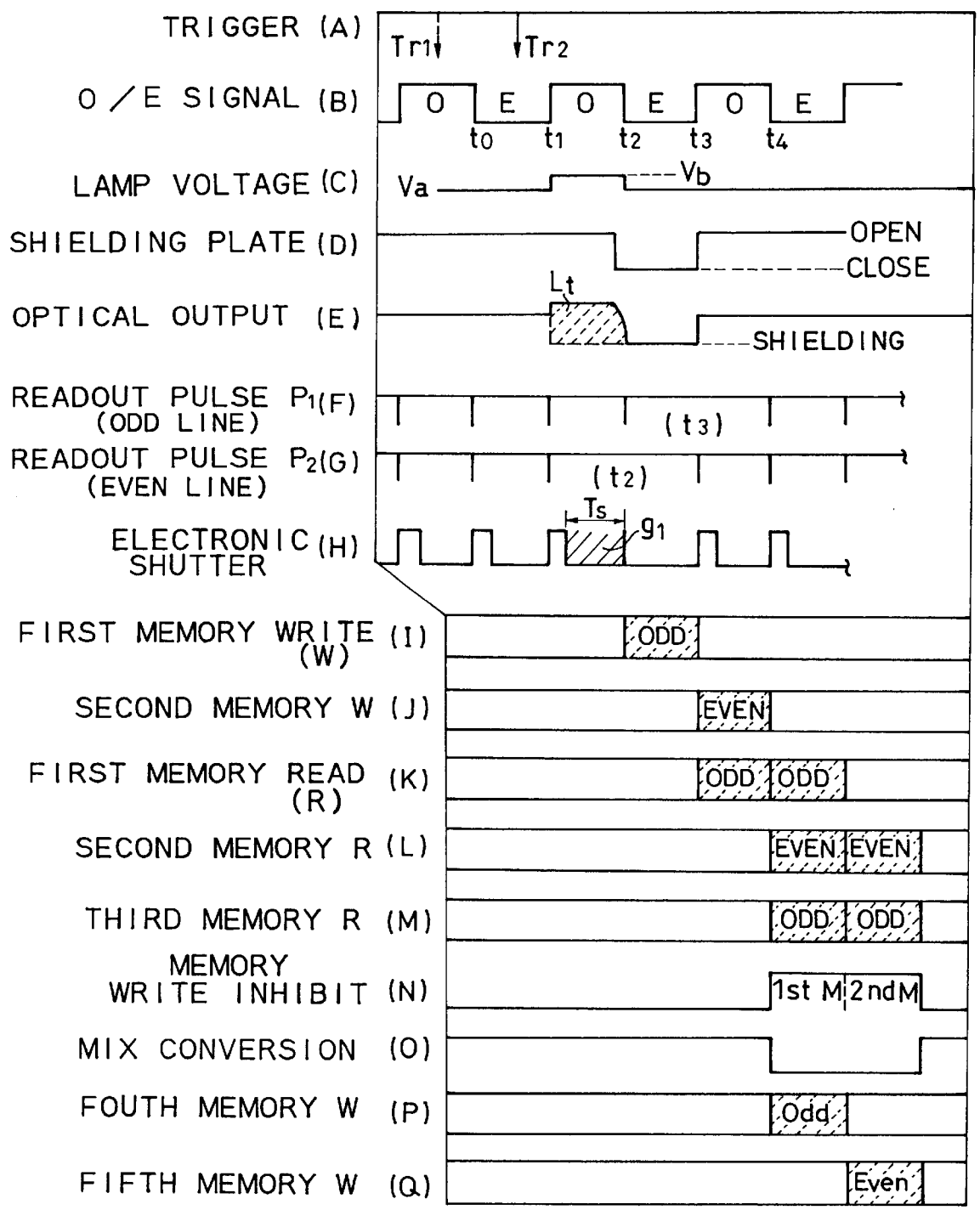
FIG. 4 is a waveform diagram showing a still image formation operation performed when the light quantity is insufficient according to the embodiment.

The first embodiment is constructed as described above, and the operation will be described with reference to FIGS. 4 and 5. As shown in FIG. 4(B), a timing signal for forming a one-field image in 1/60 second is used as field O (Odd)/E (Even) signal in the same manner as before. Under normal conditions, it is set so that moving image processing, that is, the pixel mix reading system at the output of CCD is executed, the light shielding plate 36 in the foregoing FIG. 1 is arranged at a position which does not intersect light, and light from the light source 14 is irradiated from the tip end portion into the object to be observed through the light guide 15.

Figure 6:
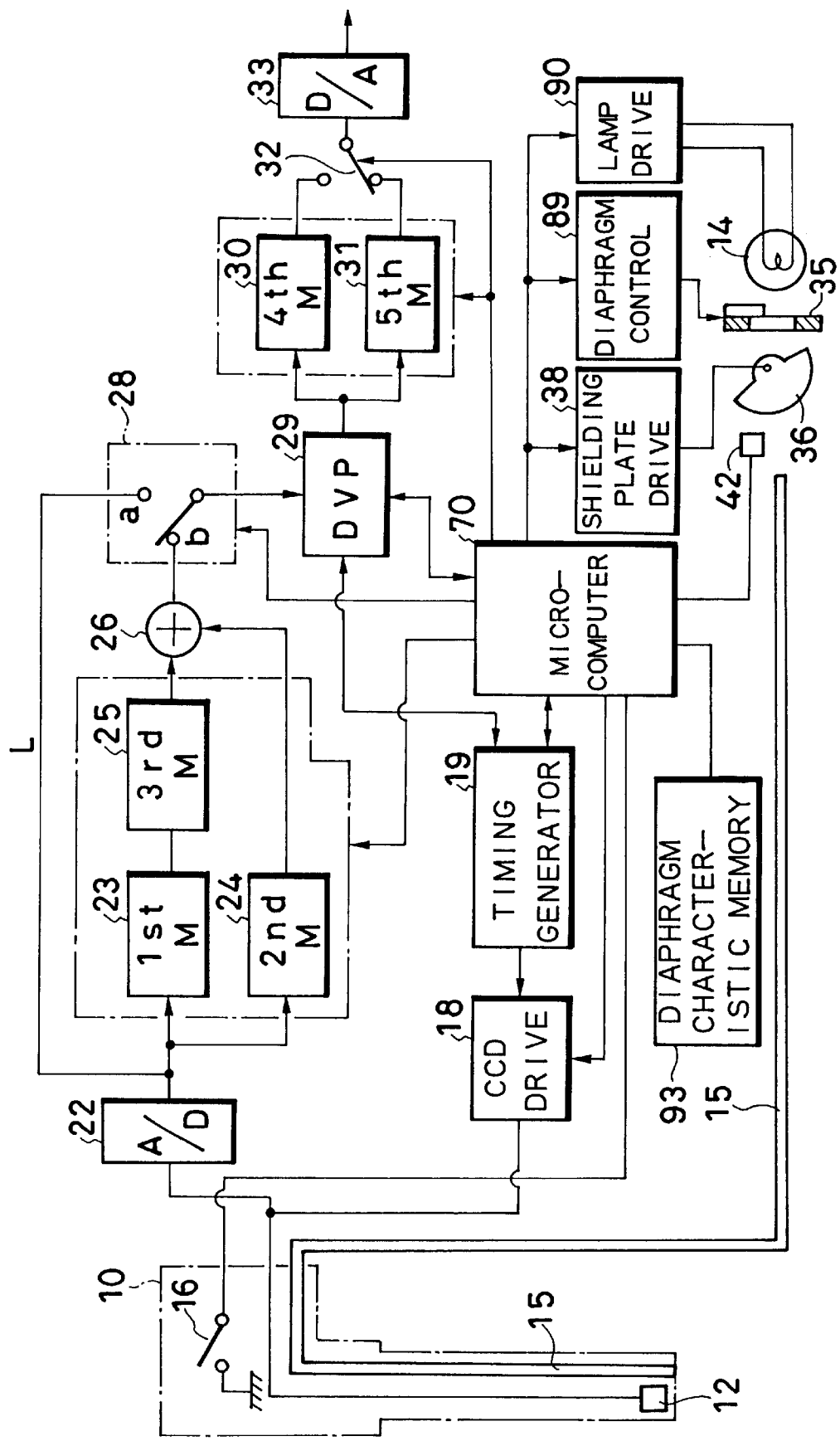
FIG. 6 is a block diagram showing the overall configuration of an electronic endoscope apparatus controlling the quantity of light according to a second embodiment of the present invention.

By this light irradiation, an image for the object to be observed is obtained in the CCD 12 at the tip end portion, and charge corresponding to the image light is accumulated in the CCD 12. Pixels between the vertical lines are added to this accumulated charge through a driving pulse from the CCD driving circuit 18 to be read out, and a pixel mixed signal described in FIG. 6 is outputted in the same manner as before. This moving image signal is supplied from an A/D converter 22 to an image switching circuit 28 through a through line L. The image switching circuit 28 then switches to the terminal "a" side to supply the moving image signal to the DVP 29. The following operation of the DVP 29 is similar to the conventional one, and the moving image is displayed on a monitor on the basis of the odd field signal stored in the fourth memory 30 and the even field signal stored in the fifth memory 31.

On the other hand, when the freeze switch 16 of the scope 10 in FIG. 1 is depressed, the microcomputer 20 switches the image switching circuit 28 to the terminal "b" side to switch the foregoing pixel mix reading system to the all-pixel reading system for still images. For example, when it is assumed that trigger Tr1 (or Tr2) due to the freeze switch 16 is given as shown in FIG. 4(A), the foregoing light shielding plate 36 obstructs the optical path only for 1/60 second before the falling (t2) following the rising (t1) of the next O/E signal [FIG. 4(D)], during which period the light is intercepted as shown in [FIG. 4(E)]. Accordingly, image data, whose all pixels are read out, become charge accumulated in CCD 12 by exposure Lt during the immediately preceding period of 1/60 second to the period of time during which the light has been intercepted.

That is, FIG. 4(F) is a read pulse P1 on the ODD line shown in FIG. 2(B), FIG. 4(G) is a read pulse P2 on the EVEN line shown in FIG. 2(C), and through the read pulse P1 without a pulse at time t3 and the read pulse P2 without a pulse at time t2 as shown, the ODD line data and EVEN line data can be successively read out from the CCD 12. Accordingly, the ODD line is read out during the foregoing light shielding period (t2 to t3), and the EVEN line is read out during the next period (t3 to t4).

FIG. 4(H) shows an electronic shutter pulse that sweeps away charges accumulated during the rise period while reading out charges accumulated during the fall period. Thus, strictly speaking, the still-image data (accumulated charges) is obtained by the exposure for a portion g1 after the charges have been swept away, and the CCD driving circuit 18 reads out the charges for all these pixels. In addition, sweeping is not executed during the light shielding period (t2 to t3) after g1.

Figure 5:
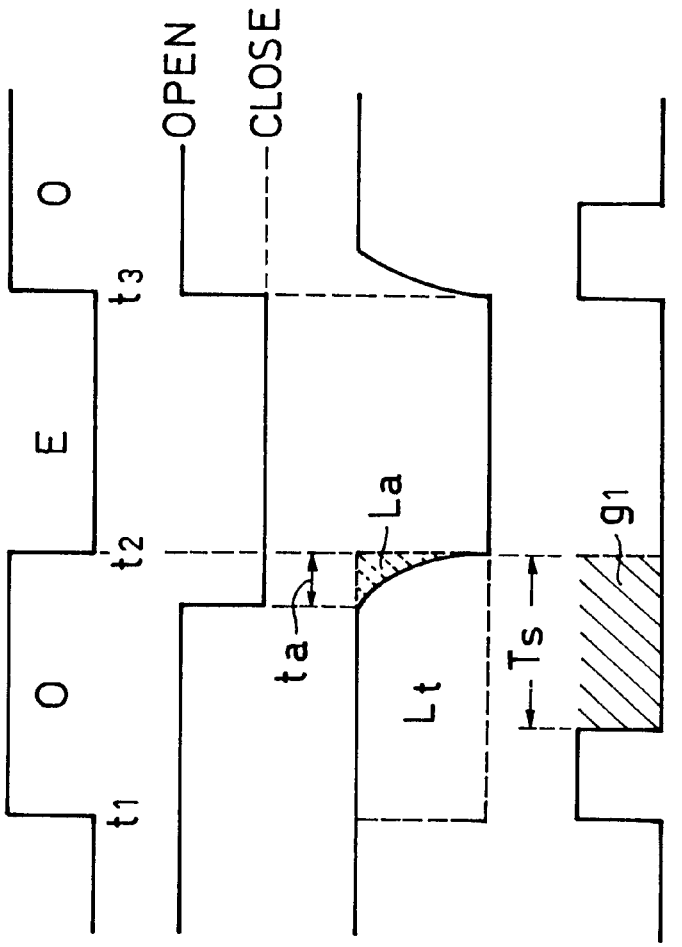
FIG. 5 is an enlarged waveform diagram showing part of the operation in FIG. 4.

During the light shielding period, unwanted charges must be prevented from accumulating in the CCD 12 to establish a complete shielding condition, so the shielding plate is controlled as shown in FIG. 5. This figure is an enlarged view of part of FIG. 4(B, D, E, H). Taking into account the mechanical response delay time ta of a driving section (gears) of the light shielding plate 36, a pulse is formed so as to be inverted earlier by the time ta. Thus, when the light shielding plate 36 is driven, light from the light source unit attenuates in a quadratic-curve manner during the response period ta before the complete light shielding condition is established. Consequently, an optical output Lt (t1 to t2) for a still image is subjected to a loss corresponding to a light quantity La, so as shown in FIG. 4(G), the light quantity is less than a required level by La even in the exposure in the section g1 obtained during an actual charge accumulation time Ts, in contrast to moving images.

Thus, this example controls the outgoing light quantity Lt during the period between t1 and t2 to be larger than that obtained when a moving image is selected. As shown in FIG. 4(C), the lamp voltage set by the lamp driving circuit 40 is controlled to increase from a voltage Va=13 V for moving images to a voltage Vb=13.4 V only during the period between t1 and t2. Accordingly, as shown in FIG. 4(E), the optical output Lt during this period also increases to enable compensation for the shortage of light quantity [La in FIG. 5(D)] in the actual charge accumulation section (the period Ts) shown in FIG. 4(H).

In such light quantity control, the lamp characteristics detection mode of the lamp 14 is executed periodically or upon the replacement of the lamp. If, for example, a secular change occurs or the burnt-out main lamp is replaced by an emergency lamp, the lamp characteristics are stored in the memory 43 after the change. If, for example, the characteristic changes to the one 102 shown in FIG. 3, the current table data is updated to the one for the characteristic 102 for storage, so that the lamp voltage Va of the lamp 14 at the reference light quantity value of 128 is 13.3 V while the lamp voltage Vb at the light quantity value of 154 that is larger than the reference value by 20% is 13.8 V. Thus, in this case, the lamp voltage is set at 13.8 V when a still image is selected in order to compensate for the lack of light quantity La.

The ODD and EVEN line data obtained from the CCD12 using this exposure control are written to the first and second memories 23 and 24 as shown in FIGS. 4(I) and 4(J), respectively, under the control of the microprocessor 20. Next, as shown in FIGS. 4(K) and 4(L), the ODD line data of the first memory 23 and the EVEN line data of the second memory 24 are read out twice each respectively, and the ODD line data are stored in the third memory 25 in order to adjust the phase of 1/60 second. Accordingly, as understood from FIGS. 4(L) to 4(M), the data for the ODD line and those for the EVEN line are to coincide in phase (timing).

Each data read out from the foregoing memories 25 and 24 in this way is pixel-mixed by the mixing circuit 26, and in order to enable this pixel mixing to be performed in this example, the first memory 23 and the second memory 24 are write-inhibited as shown in FIG. 4(N). In the same period as this, the pixels are mixed and converted [FIG. 4(O)], and added data of 0-line+1-line, 2-line+3-line, . . . shown in FIG. 2(D) are first outputted, and are stored in the fourth memory 30 as the Odd field data [FIG. 4(P)]. Next, added data of 1-line+2-line, 3-line+4-line, . . . shown in FIG. 2(E) are outputted, and are stored in the fifth memory 31 as the Even field data [FIG. 4(Q)].

The moment when these Odd field data and Even field data are read out, a switching circuit 32 selects the fourth memory 30 and the fifth memory 31 so that each field data is alternately outputted. These field data are outputted to the monitor through a D/A converter 33, and are image-displayed on the monitor through interlaced scanning. As a result, as regards still images, the images will be displayed on the basis of the all pixel data obtained during the same exposure, and images with high image-quality can be obtained. Therefore, even if there is any shake of the endoscope itself in 1/60 second or any movement of the object to be observed, it, it becomes possible to observe a sharp still image less affected by it.

Advantageously, this example can faithfully reproduce motions of an object by allowing the CCD12 to use the mix reading method for moving images. Of course, to obtain clearer moving images without blurring, the all-pixel reading method using the diaphragm 35 and the diaphragm controlling circuit 39 can be used for image formation.

The lamp characteristic detection mode may be executed upon the replacement of the lamp or periodically (using an operation switch), as described above, but this may be automatically carried out. For example, if an emergency lamp is provided in the apparatus and when it is detected that the main lamp has been burnt out and that the replaced emergency lamp is normal, the apparatus is automatically controlled to shift to the lamp characteristic detection mode.

In addition, instead of fixed installation, the optical sensor 42 may be mounted at a predetermined position of the apparatus so as to electrically connect thereto only when the lamp characteristics are to be detected.

As described above, the first embodiment can control the lamp voltage to compensate for the lack of light quantity caused by a delayed operational response from the shielding means. In addition, the shortage of light quantity can be compensated for appropriately depending on the type of the lamp, differences among different types of lamps, and secular changes.

Second Embodiment

FIG. 6 shows a configuration of an electronic endoscope according to Embodiment 2. This embodiment controls the diaphragm to compensate for insufficient light quantity using the all-pixel reading method. The basic configuration of the apparatus shown in FIG. 6 is similar to that in FIG. 1, and the CCD driving circuit 18 inputs a timing signal under the control of the microcomputer 20 to control the driving of the pixel mix reading system at the output of CCD for moving images and of the all-pixel reading system for still images. The microcomputer 70 provides comprehensive controls and executes light quantity control, which will be described below.

In addition, the light source includes a diaphragm driving circuit 89 for driving the diaphragm 35, a lamp driving circuit 90 for controlling the turn-on and -off of the lamp 14, and the optical sensor (photo transistor) 42 for measuring the quantity of outgoing light from the light source. Furthermore, a characteristic memory (EPROM or RAM) 93 is connected to the microcomputer 70 to store table data (characteristic data) indicating the relationship between the quantity of outgoing light from the light source and the diaphragm value. The optical sensor 42 may be fixedly installed but may be mounted at a predetermined position of the apparatus so as to electrically connect thereto only when the characteristics of the diaphragm value are to be detected.

The diaphragm driving circuit 89 drives the diaphragm 35 so as to set the image brightness at a predetermined value based on an illuminance control signal, and uses the table data to variably control the diaphragm 35 in order to compensate for the lack of light quantity when a still image is selected. That is, an illuminance signal obtained by the DVP 29 is supplied to the microcomputer 70, which then provides the diaphragm driving circuit 89 with an illuminance control signal for setting the image brightness at a predetermined value, thereby driving the diaphragm 35 to adjust the quantity of outgoing light from the light source.

In addition, in this apparatus, diaphragm characteristic data is stored in the characteristic memory 93 prior to shipment. For example, the diaphragm driving circuit 89 varies the diaphragm controlling voltage among 200 levels (the number of control levels is arbitrary) between V1 and V200 (the numerical aperture of the diaphragm increases with the increasing number of the control voltage), and the optical sensor 42 then detects the quantity from outgoing light from the light source to create table data (data sequence table) consisting of a diaphragm characteristic curve 201 such as that shown in FIG. 7. The detected light quantity value is represented by digital values ranging from 0 to 255, and table data of diaphragm values (voltages V1 to V200) required to obtain the 255 light quantity values is stored in the characteristic memory 93.

The microcomputer 70 calculates a light quantity value required to compensate for the lack of light quantity, from the current diaphragm controlling voltage Vc supplied when the freeze switch is depressed, and reads out a diaphragm controlling voltage Vd required to obtain this light quantity value. If, the lack of light quantity is, for example, about 20% when a still image is selected and if the current controlling voltage Vc is V40 when the freeze switch is depressed as shown in FIG. 7, the diaphragm controlling voltage V49 at the light quantity value of 120 larger than the value of 100 by 20% is read out from the characteristic memory 93 as the voltage Vd.

The microcomputer 70 supplies the data for the controlling voltages Vc and Vd to the diaphragm driving circuit 89. Thus, when the freeze switch 16 is depressed, the diaphragm controlling voltage is increased, for example, from V40 to V49 to increase the quantity of outgoing light from the light source for a predetermined period of time (one field). This operation compensates for the shortage of light quantity caused by a delayed response from the shielding plate 36 for the next shielding period.

Figure 7:
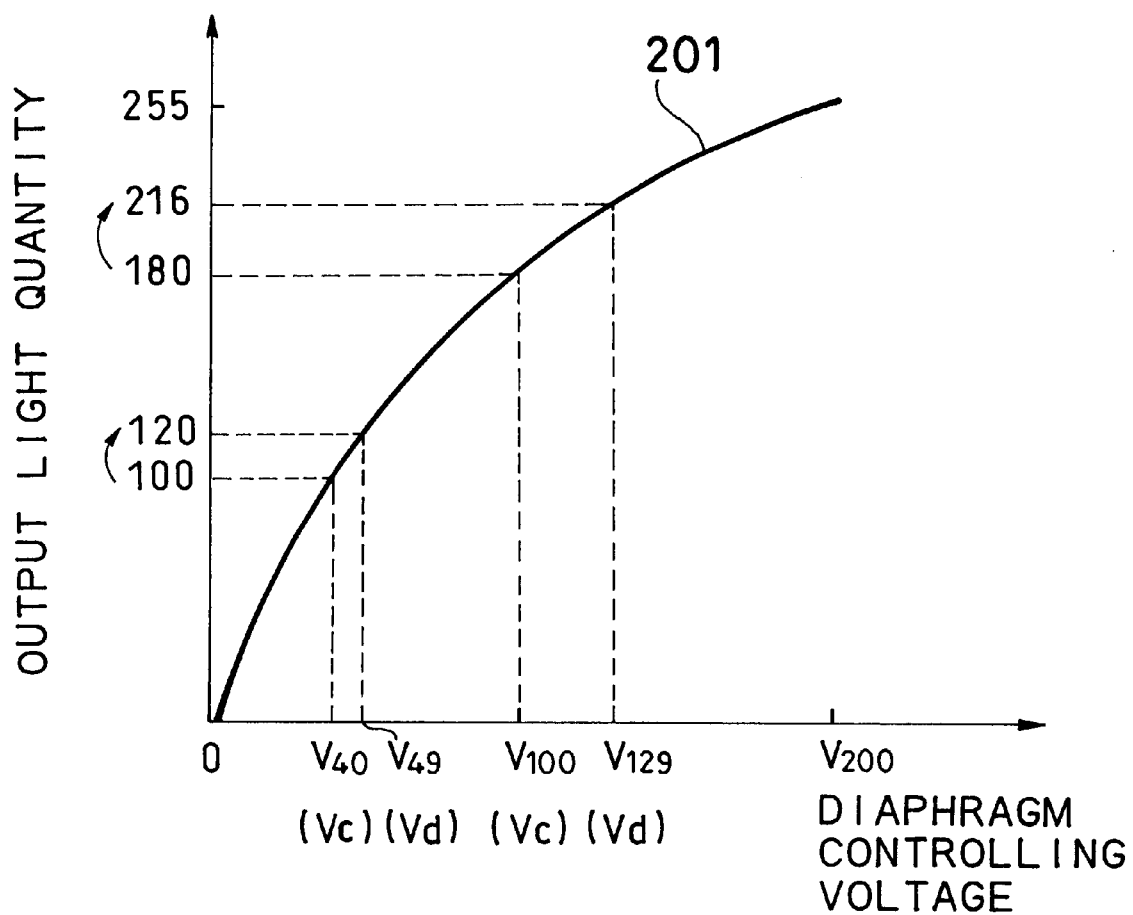
FIG. 7 is a graph showing a diaphragm characteristic according to the second embodiment.

If the diaphragm 35 is installed only to compensate for the lack of light quantity without executing control for maintaining the image brightness at a predetermined value, the characteristic memory 93 may store only the diaphragm controlling voltage Vc at the light quantity value required when a moving image is selected and the diaphragm controlling voltage Vd at the light quantity value required when a still image is selected, instead of the characteristic table data (data sequence table) shown in FIG. 7.

Figure 8:
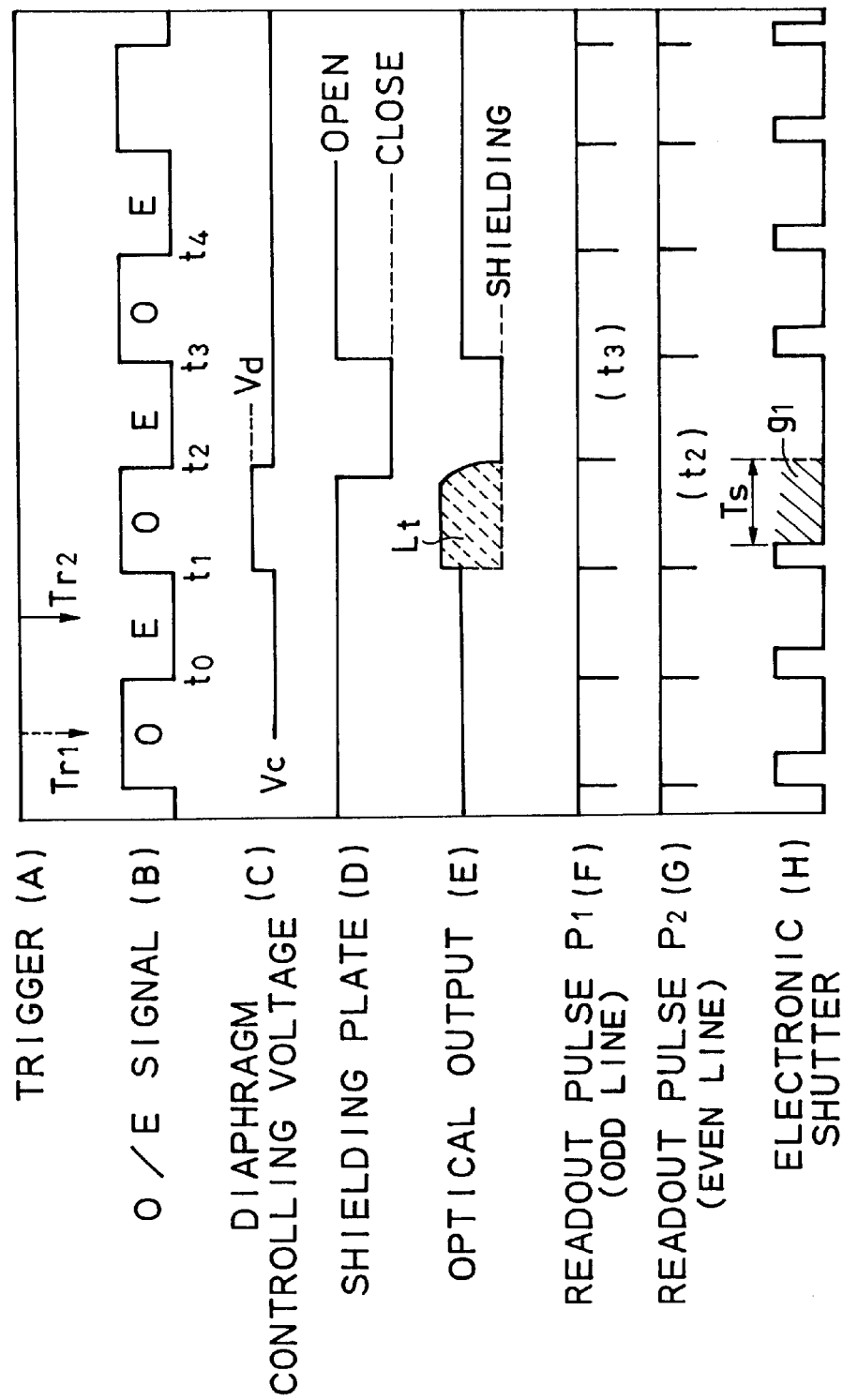
FIG. 8 is a waveform diagram showing a still image formation operation according to the second embodiment.
Figure 9:
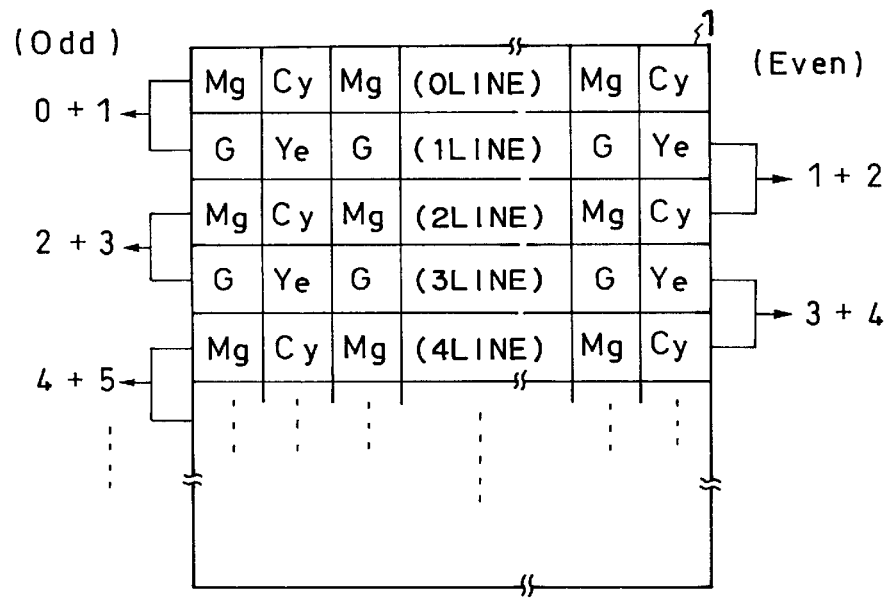
FIG. 9 describes a configuration of a color filter and a pixel mix readout according to a conventional CCD.
Figure 10:
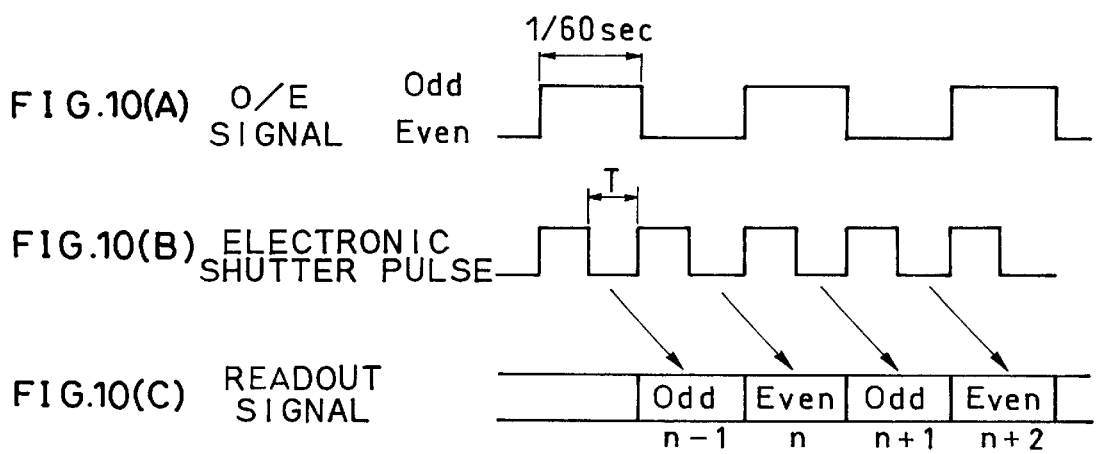
FIG. 10 is an explanatory drawing showing an operation performed by a conventional CCD.

The second embodiment is configured as described above, and its basic operation is similar to that of the first embodiment and is partly shown in FIG. 8. In this case, the apparatus is also normally set to execute moving image processing, that is, the pixel mix reading system at the output of CCD, the shielding plate 36 in FIG. 6 is placed so as not to intercept light, and the CCD12 adds pixel signals in vertically arranged lines together and reads them out to display a moving image on a monitor.

On the other hand, when the freeze switch 16 of the scope 10 shown in FIG. 6 is depressed, the microcomputer 70 switches the image switching circuit 28 to the terminal "b" side to switch the image mix reading system to the all-image reading system for still images. When, for example, a trigger Tr1 (or Tr2) is provided using the freeze switch 16 as shown in FIG. 8(A), the light shielding plate 36 intercepts the optical path for about 1/60 second immediately before t2 in FIG. 8(B) [FIG. 8(D)], and during this period, the optical output from the light source unit is intercepted, as shown in FIG. 8(E). Thus, image data for which all pixels are read out is charges accumulated by the CCD12 using the optical output Lt during the 1/60-second period immediately before the shielding period. The readout pulses are P1 and P2 shown in FIGS. 8(F) and (G), and for the accumulated charges obtained by the exposure in the section g1 shown in FIG. 8(H), odd lines are read out during the shielding period (between t2 and t3), while even lines are read out during the subsequent period (between t3 and t4).

As described in FIG. 5 for the first embodiment, taking into account a delay time ta in a mechanical response from the driving section of the shielding plate 36, a shielding plate controlling pulse is formed so as to be inverted earlier by this time Ta, resulting in a loss corresponding to a light quantity La in the optical output Lt as shown in FIG. 5(E). Thus, based on the diaphragm characteristic table data stored in the characteristic memory 93, the second embodiment provides control such that the optical output Lt during the period between t1 and t2 is higher than in moving images. That is, as shown in FIG. 7, if the current diaphragm controlling voltage Vc is V100 when the freeze switch 16 is depressed, the diaphragm controlling voltage Vd providing the light quantity value of 216 that is larger than the value of 180 by 20% is read out from the characteristic memory 93 and delivered to the diaphragm driving circuit 89. FIG. 8(C) shows this situation, and the diaphragm controlling voltage during the period between t1 and t2 is set at Vd that is higher than Vc for moving images to increase the numerical aperture of the diaphragm 35 by 20%. Consequently, as shown in FIG. 8(E), the optical output Lt during this period also increases to enable compensation for the lack of light quantity in the actual charge accumulation section g1 (period Ts) for the still image shown in FIG. 8(H).

The odd line data obtained from the CCD12 using this exposure control is written to the first and second memories 23 and 24 under the control of the microcomputer 70, and the subsequent operation is similar to that in FIG. 4. That is, for a still image, the image is displayed based on the all-pixel data obtained during the same exposure, resulting in an optimally bright high-quality data. For a moving image, motions of an object can be reproduced faithfully.

What is claimed is:

1. An electronic endoscope apparatus controlling the quantity of light, comprising:

a light source for irradiating an observed object with light;

outgoing light quantity varying means for variably adjusting the quantity of outgoing light from the light source based on a predetermined control value;

shielding means for intercepting light from said light source to set a shielding period for an all-pixel reading system;

a signal processing circuit for executing the all-pixel reading system that uses said shielding period to read out signals for all the signals accumulated in an image pickup device during a single exposure;

storage means for storing characteristic data between said control value and said quantity of outgoing light; and light quantity controlling means for controlling said outgoing light quantity adjusting means based on the characteristic data stored in the storage means to adjust the quantity of outgoing light from said light source, thereby compensating for the lack of light quantity caused by a delayed response from said shielding means for a shielding operation.

2. An electronic endoscope apparatus controlling the quantity of light according to claim 1, wherein:

said outgoing light quantity varying means comprises a lamp driving means for varying a lighting voltage for a light source lamp, said storage means storing the characteristic data between the lighting voltage for said light source lamp and said quantity of outgoing light, said light quantity controlling means varying the lighting voltage for said light source lamp based on the characteristic data stored in said storage means to adjust the quantity of outgoing light from said light source, thereby compensating for the lack of light quantity caused by a delayed response from said shielding means for a shielding operation.

3. An electronic endoscope apparatus controlling the quantity of light according to claim 2, wherein a light quantity sensor for detecting the quantity of outgoing light from said light source is provided to store in said storage means the characteristic data between said lamp lighting voltage and said outgoing light quantity based on an output from the light quantity sensor.

4. An electronic endoscope apparatus controlling the quantity of light according to claim 3, wherein said light quantity controlling means executes a lamp characteristic detection mode that uses said optical sensor to automatically create and store the characteristic data on said lamp lighting voltage.

5. An electronic endoscope apparatus controlling the quantity of light according to claim 1, wherein said outgoing light quantity varying means comprises a diaphragm for adjusting the quantity of outgoing light from a light source lamp, said storage means storing the characteristic data between the diaphragm value of said diaphragm and said quantity of outgoing light, said light quantity controlling means varying the numerical aperture of said diaphragm based on the characteristic data stored in said storage means to adjust the quantity of outgoing light from said light source, thereby compensating for the lack of light quantity caused by a delayed response from said shielding means for a shielding operation.

6. An electronic endoscope apparatus controlling the quantity of light according to claim 5, wherein a light quantity sensor for detecting the quantity of outgoing light from said light source is provided to store in said storage means the characteristic data between said diaphragm value and said outgoing light quantity based on an output from the light quantity sensor.

7. An electronic endoscope apparatus controlling the quantity of light according to claim 6, wherein said light quantity controlling means executes a diaphragm-value characteristic detection mode that uses said optical sensor to automatically create and store the characteristic data on said diaphragm value.

8. An electronic endoscope apparatus controlling the quantity of light, comprising:

a light source for irradiating an observed object with light;

outgoing light quantity varying means for variably adjusting the quantity of outgoing light from the light source based on a predetermined control value;

shielding means for intercepting light from said light source to set a shielding period for an all-pixel reading system;

a signal processing circuit for executing a pixel mix reading system at the output of the image pickup device for mixing together pixels accumulated in said image pickup device in such a way that vertically arranged lines are mixed together and then outputting the resulting pixels to form a moving image and an all-pixel reading system for forming a still image by using said shielding period to read out all pixels accumulated in the image pickup device during a single exposure;

storage means for storing characteristic data between said control value and said quantity of outgoing light; and light quantity controlling means for controlling said outgoing light quantity adjusting means based on the characteristic data stored in the storage means to adjust the quantity of outgoing light from said light source, thereby compensating for the lack of light quantity caused by a delayed response from said shielding means for a shielding operation.

* * * * *